United States Patent

Nakano et al.

[11] Patent Number: 5,811,660
[45] Date of Patent: Sep. 22, 1998

[54] AIR-FUEL RATIO SENSING ELEMENT

[75] Inventors: Syuichi Nakano, Kariya; Tomio Sugiyama, Nagoya; Shinichiro Imamura, Kariya; Hiromi Sano, Nagoya, all of Japan

[73] Assignee: Denso Corporation, Kariya, Japan

[21] Appl. No.: 748,826

[22] Filed: Nov. 14, 1996

[30] Foreign Application Priority Data

Nov. 15, 1995 [JP] Japan ................................... 7-322158
Oct. 15, 1996 [JP] Japan ................................... 8-293312

[51] Int. Cl.⁶ .................................................. G01M 15/00
[52] U.S. Cl. ........................ 73/23.32; 73/31.05; 701/109
[58] Field of Search ................................ 73/23.31, 23.32, 73/118.1, 118.2, 116, 117.2, 117.3, 31.05, 31.06; 364/431.051, 431.062; 701/103, 109

[56] References Cited

U.S. PATENT DOCUMENTS

| | | | |
|---|---|---|---|
| 4,298,573 | 11/1981 | Fujishiro | 73/23.32 |
| 4,772,376 | 9/1988 | Yukawa et al. | 204/410 |
| 5,591,321 | 1/1997 | Pyke | 73/31.06 |

FOREIGN PATENT DOCUMENTS

| | | |
|---|---|---|
| 63-61945 | 3/1988 | Japan . |
| 2-198352 | 8/1990 | Japan . |
| 4-120454 | 4/1992 | Japan . |
| 6-258278 | 9/1994 | Japan . |

Primary Examiner—George M. Dombroske
Attorney, Agent, or Firm—Cushman Darby & Cushman IP Group of Pillsbury Madison & Sutro LLP

[57] ABSTRACT

An air-fuel ratio sensing element comprises a pump cell having at least one pair of pump electrodes thereon, a sensor cell having at least one pair of sensor electrodes thereon, and a gas chamber having two surfaces defined by the pump cell and the sensor cell. Two to five gas holes, each having approximately the same diameter and communicating with the gas chamber, are provided for introducing sensed gas into the gas chamber. The gas holes form their projection images on the surface of the sensor cell which has a sensor electrode thereon and faces the gas chamber. The sensor electrode is shaped such that it is dividable into a plurality of similar subsections defined by virtual lines connecting the geometric centroid of the sensor electrode and the center of the projection image of each gas hole.

13 Claims, 15 Drawing Sheets

AIR-FUEL RATIO SENSING ELEMENT

BACKGROUND OF THE INVENTION

1. Field of the Invention

This invention relates to an air-fuel ratio sensing element preferably used for detecting the concentration of a particular gas component in the exhaust gas passage of an internal combustion engine or the like.

2. Related Art

Emission gas exhausted from an automotive vehicle has recently been severely restricted and reduction in the amount of harmful components will be more strictly required in the future. Accordingly, exhaust gas purification efficiency must be improved. As one method for improving the purification efficiency of the exhaust gas, the air-fuel ratio of a fuel mixture needs to be accurately controlled before being introduced into an internal combustion engine.

To realize an ideal or theoretical air-fuel ratio, an air-fuel ratio sensing element is usually installed in the exhaust gas passage of the internal combustion engine of the automobile. The fuel amount supplied to the combustion chamber of the internal combustion engine can be precisely feedback controlled in accordance with the output of the air-fuel ratio sensing element equipped in the exhaust gas passage.

One conventional air-fuel ratio sensing element incorporates an oxygen ion conductive solid electrolyte. This air-fuel ratio sensing element comprises a pump cell having pump electrodes, a sensor cell having sensor electrodes, and a gas chamber defined between these two cells. Numerous gas holes are provided on the pump electrode for introducing gas into the gas chamber. In such a gas concentration sensing element, appropriate gas diffusion techniques are normally required. The gas holes on the pump electrode can be effective to diffuse the gas. Alternatively, the pump cell may act as the gas diffusion means. In one embodiment, sensor cell and the pump cell are made of zirconia solid electrolyte.

In the above-described air-fuel ratio detecting element, the air-fuel ratio of the sensed gas can be measured by detecting the oxygen concentration in the sensed gas. Part of the sensed gas diffuses into the gas chamber through the gas diffusion means. The voltage applied between the pump electrodes is controlled by monitoring the electromotive force acting on the sensor cell, such that the oxygen concentration of the sensed gas becomes a constant value in the gas chamber.

In this operation, the pump cell creates pump current according to its oxygen pump function. The magnitude of pump current depends on the oxygen concentration of the sensed gas. Accordingly, by measuring the pump current, one can measure the oxygen concentration of the sensed gas.

To realize a highly accurate and responsive air-fuel ratio sensing element, it is necessary to eliminate any dispersion in the diffusion of the sensed gas and to prevent any undesirable gradational distribution in the sensed gas concentration along the surface of the sensor electrode.

Furthermore, to evenly diffuse the sensed gas, it is essential to reduce the flow resistance through the gas diffusion means. This is accomplished by providing gas holes communicating with the gas chamber rather than adopting a porous layer.

From the above reason, most conventional air-fuel ratio sensing elements incorporate numerous gas holes on the pump electrodes. However, the conventional air-fuel ratio sensing element does not have a good response in sensing the variation of oxygen concentration of the sensed gas.

Furthermore, forming numerous gas holes on the pump electrodes necessarily requires reducing the diameter of each gas hole, resulting in time-consuming precise machining operations during manufacturing. As a result, as the diameter of the gas holes decreases, the flow resistance generally increases. Increased flow resistance causes delays in the gas diffusion time, leading to the deterioration of the sensitivity and the response of the air-fuel ratio sensing element.

When one gas hole is employed, the sensed gas diffuses in radial directions about this single gas hole, which causes undesirable gradational distribution in its concentration between the near side and the far side of the projection image of this single gas hole.

According to the conventional art, as shown in FIG. 23, the center of gas hole projection image 80 projected on the surface of a sensor cell 92 coincides with the geometric centroid 921 of a sensor electrode 920, and the sensor electrode 920 does not overlap the gas hole projection image 80. (Refer to the Unexamined Japanese patent application No. 63-61945). The sensed gas is diffused in radial directions about the gas hole projection image 80 and then reaches the region of sensor electrode 920. This arrangement may be effective to eliminate the above-described undesirable gradational distribution in the sensed gas concentration at least in the region of sensor electrode 920, preventing overshoot in the transitional response output triggered by a change in the air-fuel ratio of the sensed gas.

However, this conventional air-fuel ratio sensing element has a drawback in its response time because the sensor electrode 920 is spaced a predetermined distance far from the gas hole projection image 80. To avoid deterioration of response characteristics, it is possible to reduce the size of sensor electrode 920, but such size reduction results in an undesirable decline of the sensor output and increases the resistance of sensor cell 92.

SUMMARY OF THE INVENTION

Accordingly, in view of above-described problems encountered in the related art, a principal object of the present invention is to provide an air-fuel ratio sensing element having excellent accuracy and response.

In order to accomplish this and other related objects, the present invention provides an air-fuel ratio sensing element having various aspects which will be described herein.

An air-fuel ration sensing element, in accordance with the first aspect of the present invention, comprises a pump cell (11) having at least one pair of pump electrodes (110) thereon, a sensor cell (12) having at least one pair of sensor electrodes (120) thereon, and a gas chamber (130) having two surfaces defined by the pump cell and the sensor cell. Two to five gas holes (2), communicating with the gas chamber, are provided for introducing sensed gas into the gas chamber. The gas holes are substantially identical in size. When the gas holes are projected perpendicularly to the surface of the sensor cell, they form gas hole projection images (20) on a surface of sensor cell. The sensor electrode is shaped such that it is dividable into a plurality of similar subsections (21–22; 21–23; 21–24; 21–25) by virtual lines connecting the geometric centroid (121) of the sensor electrode and the center (200) of the projection image of each gas hole.

According to the features of preferable embodiments of the present invention, the subsections (21–22; 21–23; 21–24; 21–25) of the sensor electrode satisfy the following relationship:

$$S/s \leq 1.25$$

where S represents the area of the largest subsection and s represents the area of the smallest subsection.

Furthermore, it is preferable that at least part of the projection image (20) of each gas hole (2) exists within the region of the sensor electrode (120). Otherwise, the entire projection image (20) of each gas hole (2) is formed on the sensor electrode (120).

An air-fuel ratio sensing element, in accordance with the second aspect of the present invention, comprises a pump cell (11) having at least one pair of pump electrodes (110) thereon, a sensor cell (12) having at least one pair of sensor electrode (120) thereon, and a gas chamber (130) having two surfaces defined by the pump cell and the sensor cell. Two to five gas holes (2) communicate with the gas chamber for introducing sensed gas into the chamber. The gas holes are substantially identical in size. The gas holes form projection images (FIG. 20, a–d) on a surface of the sensor cell, when the gas holes are projected perpendicularly to the surface of the sensor cell. These gas holes cooperatively define a maximum configuration when lines running through the individual gas hole centers are connected to each other. The maximum configuration has a geometric centroid whose projection image (51) is formed on the sensor electrode. The gas holes and the sensor electrode cooperatively satisfy the following relationship:

$$0 \leq m \leq 0.1M$$

where m represents the distance from the projection image (51) of the geometric centroid of the maximum configuration to the geometric centroid (121) of the sensor electrode, while M represents the smallest distance from the geometric centroid (121) of the sensor electrode to the periphery of the sensor electrode (120).

In the second embodiment of the present invention, the total number of the gas holes (2) is three, four or five, and the distance between arbitrarily selected two adjacent gas holes is the same as the distance between any other adjacent two gas holes. The location of gas holes satisfy the following relationship:

$$0.9L \leq 1n \leq 1.1L$$

where 1n represents the distance between any two adjacent gas holes and L represents the mean value of all the distances between adjacent two gas holes.

Furthermore, it is preferable that the cooperatively satisfy the following relationship:

$$0.88R \leq r_n \leq 1.12R$$

where $r_n$ represents the diameter of an arbitrary gas hole, while R represents the mean value of all diameters of the gas holes.

Similar to the first aspect, it is preferable that at least part of the projection image (20) of each gas hole (2) exists within the region of the sensor electrode (120). The entire projection image (20) may also exist within the region of the sensor electrode (120). As an alternative in the second aspect of the present invention the projection image (20) may exist entirely outside the region of the sensor electrode.

BRIEF DESCRIPTION OF THE DRAWINGS

The above and other objects, features and advantages of the present invention will become more apparent from the following detailed description which is to be read in conjunction with the accompanying drawings, in which.

DETAILED DESCRIPTION OF THE PREFERRED EMBODIMENTS

Figure 1:
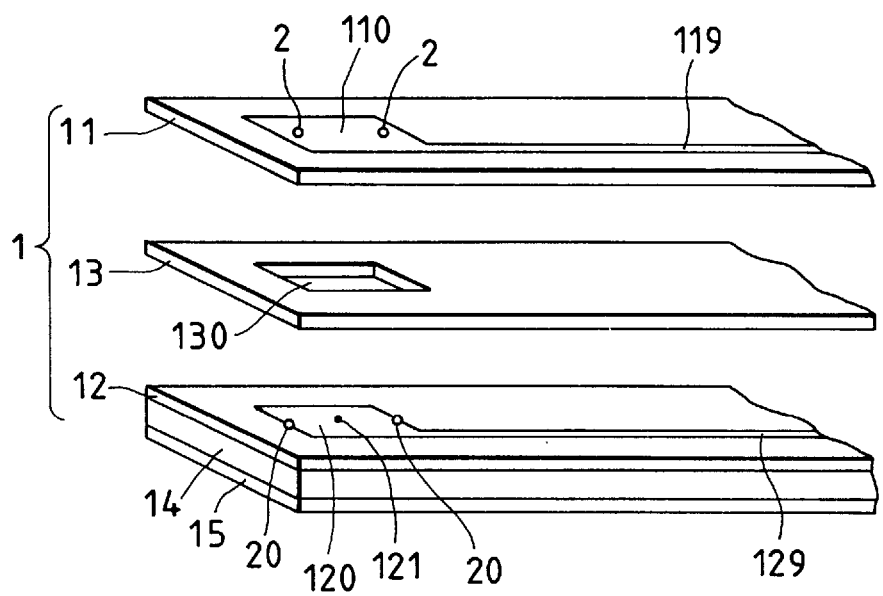
FIG. 1 is a perspective view showing the disassembled condition of an air-fuel ratio sensing element in accordance with a first embodiment of the present invention.

Preferred embodiments of the present invention will be explained in greater detail hereinafter with reference to the accompanying drawings. Identical parts are denoted by the same reference numerals throughout the views.

Embodiment 1

An air-fuel ratio sensing element in accordance with the first embodiment of the present invention will be explained with reference to FIGS. 1 through 6. The air-fuel ratio sensing element can be used for detecting the concentration of $O_2$, $NO_x$, HC and other gases.

As shown in FIGS. 1, 2, 4 and 5, air-fuel ratio sensing element 1 comprises a pump cell 11 having pump electrodes 110 provided on opposite surfaces thereof, a sensor cell 12 having sensor electrodes 120 provided on opposite surfaces thereof, and a first gas chamber 130 defined between the pump cell 11 and sensor cell 12. Pump electrode 110 has two gas holes 2 symmetrically disposed and having substantially the same area and configuration (e.g. the same diameter in the case of a circular hole). These gas holes 2 introduce the gas to be sensed into the first gas chamber 130.

Figure 2:
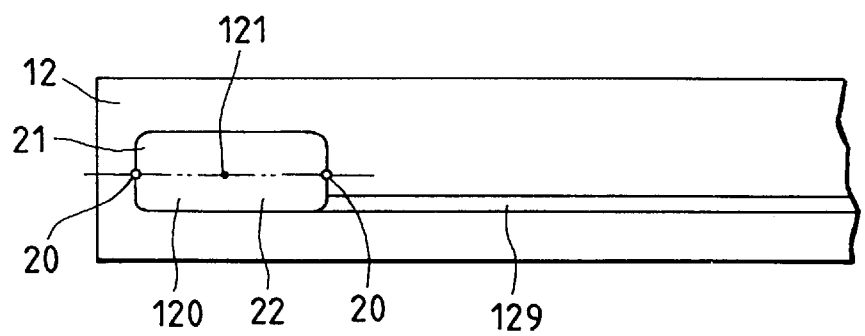
FIG. 2 is a plan view showing a sensor cell of the air-fuel ratio sensing element in accordance with the first embodiment of the present invention.

As shown in FIG. 2, the sensor electrode 120 is shaped such that it is dividable into two subsections 21 and 22 having substantially the same configuration defined by a virtual straight line passing through the geometric centroid 121 of sensor electrode 120 and the center 200 (refer to FIG. 3) of each gas hole projection image 20. In this embodiment, the gas hole projection image 20 is formed by projecting the gas hole 2 perpendicularly to the surface of sensor cell 12. It is preferable that each gas hole 2 is circular and has the ideal diameter approximately 0.2 mm, while the area of each subsection 21 or 22 is approximately 4 mm².

According to the present invention, it is preferably that the diameter of each gas hole 2 is between 0.05 and 0.6 mm, and the area of each subsection 21 or 22 is in the range of 2 to 10 mm². The sum of all the gas holes 2 is preferably in the range of 0.007 to 0.6 mm².

Figure 5:
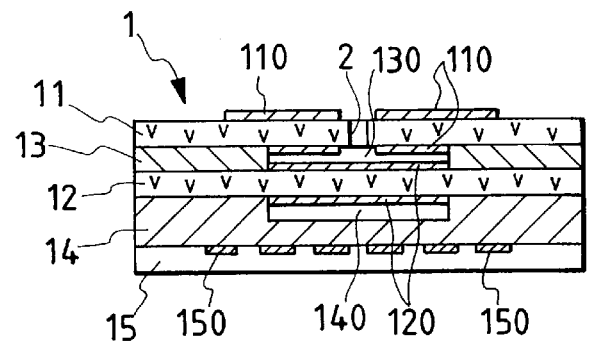
FIG. 5 is a cross-sectional view taken along a line A—A of FIG. 4.

Pump cell 11 comprises a sheet of zirconia solid electrolyte on which the pump electrode 110 is formed on opposite surfaces, as shown in FIG. 5. Each pump electrode 110 chiefly comprises heat-resisting conductive material such as platinum having electrode activity. Similarly, sensor cell 12 comprises a sheet of zirconia solid electrolyte on which sensor electrode 120 is formed on opposite surfaces, as shown in FIG. 5. Each sensor electrode 120 chiefly comprises heat-resisting conductive material.

Figure 4:
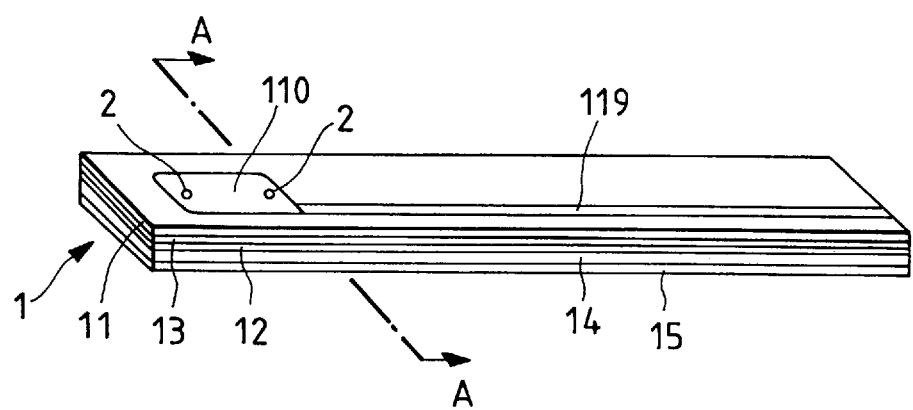
FIG. 4 is a perspective view showing the assembled air-fuel ratio sensing element in accordance with the first embodiment of the present invention.

As shown in FIGS. 1, 4 and 5, a spacer 13 is interposed between pump cell 11 and sensor cell 12. Spacer 13 is made of ceramic and has excellent heat conductivity and has a rectangular opening which in conjunction with the pump all 4 and the sensor all 12 defines the first gas chamber 130 into which gas can be introduced to detect its air-to-fuel concentration.

A ceramic duct 14 is provided beneath of sensor cell 12 which defines a second gas chamber 140 into which reference gas is introduced. A heater 15 having a plurality of heater elements 150 is provided beneath the duct 14.

Figure 6:
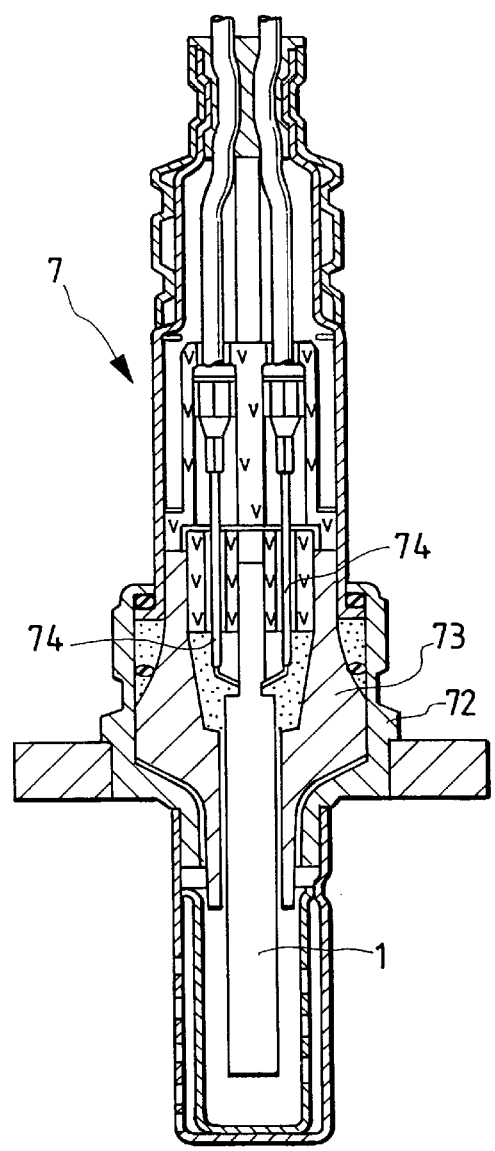
FIG. 6 is a cross-sectional view showing the air-fuel ratio detector with the air-fuel ratio sensing element installed in accordance with the first embodiment of the present invention.

As shown in FIG. 6, the air-fuel ratio sensing element 1 is installed in an air-fuel ratio detector 7 to detect the concentration of the intended component contained in the gas.

The air-fuel ratio sensing element 1 is securely housed in a housing and fixed by a ceramic insulator 73. With reference to FIGS. 1, 2 and 6, to read the sensor output from air-fuel ratio sensing element 1, lead wires 74 are spot welded to conductive heat-resisting metallic pathways 119 and 129 attached on the surface of the air-fuel ratio sensing element 1.

Another method of reading the sensor output involves providing sensor output electrodes at the end of the air-fuel ratio sensing element and bringing the metal plate terminals disposed at the distal ends of lead wires 74 into press fitting contact with these sensor output electrodes.

Figure 3:
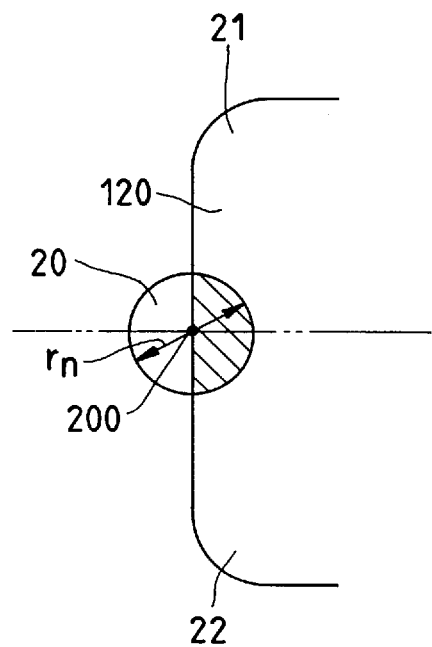
FIG. 3 is a view showing the positional relationship of the gas hole projection image on the surface of the sensor cell and a sensor electrode which is only partly projected onto the sensor electrode according to the first embodiment of the present invention.

As shown in FIG. 3, each gas hole 2 is located on the pump electrode 110 at a predetermined position where the gas hole projection image 20 on the sensor cell 12 overlaps the sensor electrode 120. Preferably, the periphery or outline of sensor electrode 120 meets the center 200 of circular gas hole projection image 20. In other words, one half (i.e. the shaded portion) of the circular gas hole projection image 20 is projected within the region of the sensor electrode 120.

As shown in FIGS. 2 and 3, the geometric centroid 121 of sensor electrode 120 coincides with the midpoint between centers 200 of two circular gas hole projection images 20.

Next, the operation and function of the above-described first embodiment of the present invention will be explained.

According to the arrangement of air-fuel ratio sensing element 1 of the first embodiment, two gas holes 2 are located at specific positions on the pump electrodes 110 as described above. These gas holes 2 should be formed having a relatively large diameter. Assurance of appropriate manufacturing accuracy in the formation of these two gas holes 2 is accomplished easier with holes with larger diameters. With larger diameters, it also becomes possible to form the gas holes 2 more uniformly.

Hence, the amount of sensed gas diffusing through each gas hole 2 can be equalized. It becomes possible to eliminate any undesirable gradational distribution in the sensed gas concentration along the surface of the sensor electrode 120.

Furthermore, gas hole projection images 20 are uniformly or symmetrically disposed with respect to sensor electrode 120. It is possible to eliminate any undesirable gradational distribution in the sensed gas concentration along the surface of sensor electrode 120. Accordingly, the air-fuel ratio sensing element 1 of the first embodiment is highly accurate.

When the concentration of a certain component (e.g. oxygen) in the sensed gas is suddenly changed, the conventional air-fuel ratio sensing element does not detect such a sudden change unless this sudden change occurs in the entire region of the sensor electrode. Because the air-fuel ratio sensing element has the tendency to cause undesirable gradational distribution in the sensed gas concentration, it is difficult to detect sudden changes of the gas concentration.

The air-fuel ratio sensing element 1 of the present invention effectively prevents the undesirable gradational distribution in the sensed gas concentration along the surface of sensor electrode 120. Therefore, the concentration of the concerned component in the sensed gas is accurately detected. Accordingly, the air-fuel ratio sensing element 1 of the first embodiment provides an improved response.

Figure 7:
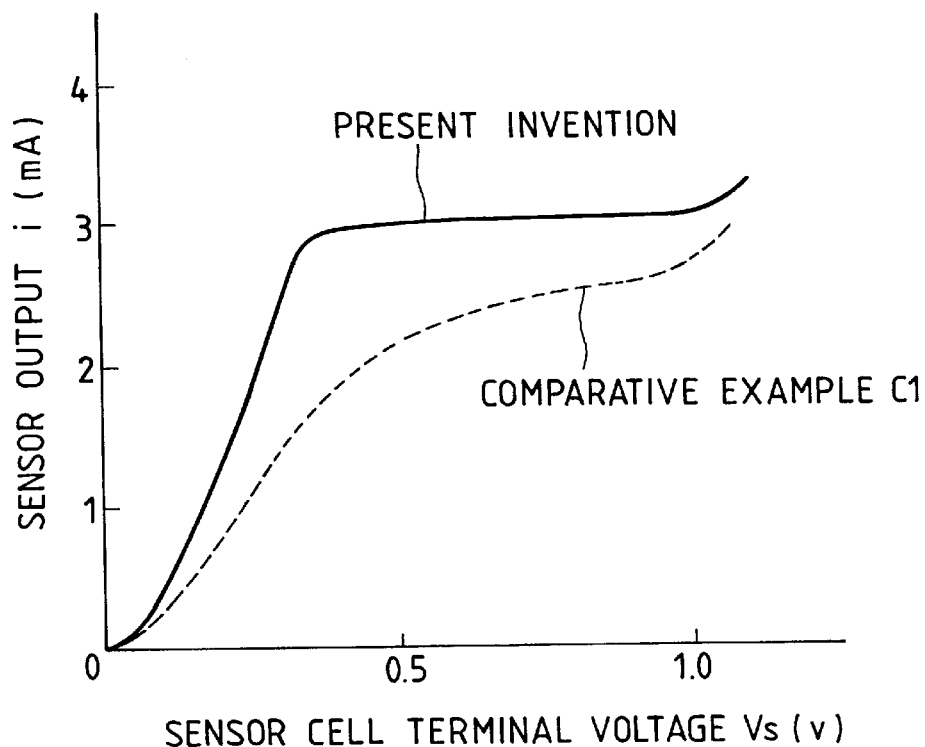
FIG. 7 is a graph showing the relationship between the terminal voltage of the air-fuel ratio sensing element and the sensor output in accordance with the first embodiment of the present invention, with a comparative example.
Figure 8:
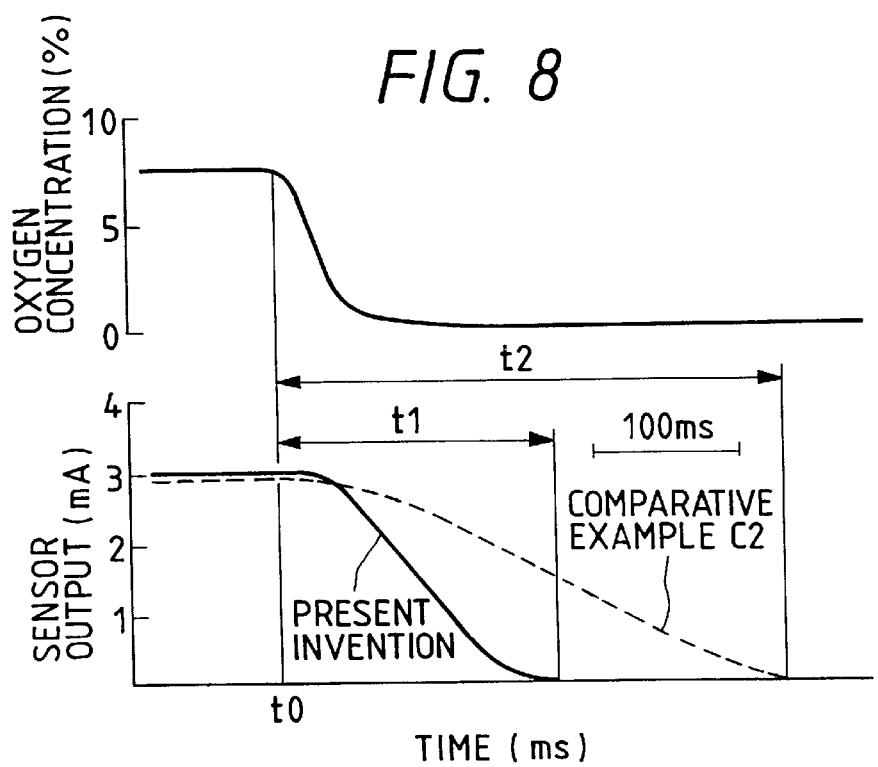
FIG. 8 is a view graph showing the relationship between the oxygen concentration of the sensed gas and the sensor output in accordance with the first embodiment of the present invention, with a comparative example.
Figure 9A:
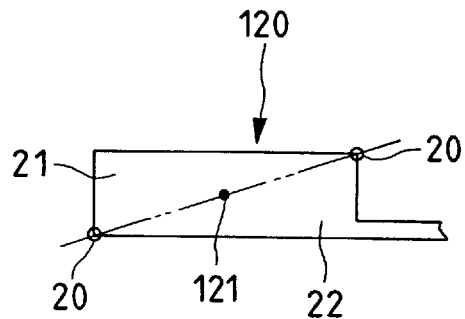
FIGS. 9A through 9D are plan views showing various modifications of sensor cells applicable to an air-fuel ratio sensing element having two gas holes in accordance with the first embodiment of the present invention.
Figure 9B:
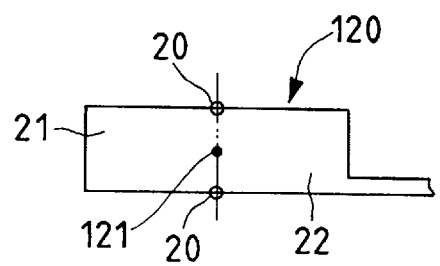
Figure 9C:
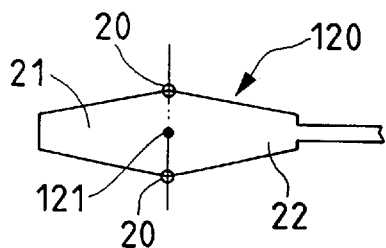
Figure 9D:
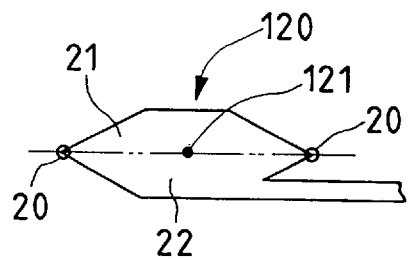

FIG. 7 shows the relationship between the terminal voltage "Vs" of the air-fuel ratio sensing element and the sensor output current "i" in accordance with the first embodiment of the present invention, with a comparative example C1. FIG. 8 shows the relationship between the oxygen concentration of the sensed gas and the sensor output in accordance with the first embodiment of the present invention, with a comparative example C2.

The comparative example C1 is an air-fuel ratio sensing element having the same configuration as the air-fuel ratio sensing element of the first embodiment. However, the gas holes of the comparative example C1, formed on the pump electrodes by a needle press machine, have diameters of 30 μm. The interval between two gas holes is 0.5 mm.

The comparative example C2 is an air-fuel ratio sensing element having the same configuration as the air-fuel ratio sensing element of the first embodiment. This comparative example C2 has only one gas hole provided on the pump electrodes at the position corresponding to its geometric centroid.

In FIG. 7, "Vs" represents the terminal voltage of sensor cell 12, while "i" represents the pump cell current which is the sensor output. The detecting portion of the element is heated at 600° C. in an atmosphere of nitrogen gas containing oxygen with a 7.5% concentration. The relationship between pump cell current "i" and sensor cell terminal voltage "Vs" is monitored while the voltage applied to the terminals of the pump cell is gradually changed.

As shown in FIG. 7, the air-fuel ratio sensing element in accordance with the present invention demonstrates an improved waveform according to which the sensor cell terminal voltage Vs varies steeply in response to a small change of pump cell current "i." This improved response occurs because the air-fuel ratio sensing element of the present invention distributes the oxygen concentration uniformly along the surface of the sensor cell electrode.

On the other hand, according to the comparative example C1, "Vs" shows a dull change in accordance with the change of the pump cell current "i", due to uneven or irregular distribution of oxygen concentration along the surface of the sensor cell electrode.

FIG. 8 shows the steep change of the oxygen concentration in the sensed gas and the change of the sensor output in the present invention as compared to comparative example C2. In this case, "Vs" is maintained at 0.45V by using a high-speed analog circuit to control the voltage applied to the pump cell. The pump cell current "i" is detected in response to the steep reduction in oxygen concentration from 7.5% to 0% in a stepwise fashion. As shown in FIG. 8, the oxygen concentration starts reducing from 7.5% to 0% at the time to. According to present invention, the sensor output quickly reaches 0 at time t1. On the other hand, according to the comparative example C2, the sensor output becomes 0 at time t2 (t1<t2). In other words, the present invention quickly responds to the changes in the oxygen concentration, when compared with the comparative example C2. Accordingly, the present invention provides an air-fuel ratio sensing element having an excellent response.

Modifications of Embodiment 1

FIGS. 9 through 12 shows various modifications of the configuration of sensor electrode 120 and the location of gas hole projection images 20 in accordance with the first embodiment of the present invention.

First, as shown in FIGS. 9A through 9D, according to the first embodiment of the present invention, it is preferable that the sensor electrode 120 has a flattened rectangular or symmetrical quadrangular configuration. Two gas hole projection images 20 are formed symmetrically as shown in the drawing.

The sensor electrode 120 is shaped so as to be dividable into two subsections 21 and 22 each having substantially the same area and configuration defined by virtual straight lines passing through the geometric centroid 121 of sensor electrode 120 and the center 200 (refer to FIG. 3) of each gas hole projection image 20. As described previously, the gas hole projection image 20 is formed by projecting the gas hole 2 perpendicularly or vertically to the sensor cell 12. The geometric centroid 121 of sensor electrode 120 coincides with the midpoint between centers 200 of two circular gas hole projection images 20.

Figure 10A:
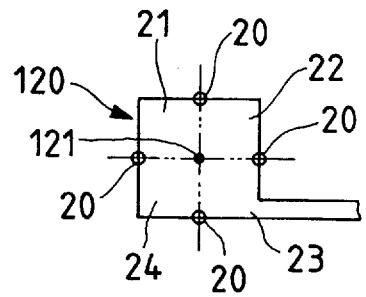
FIGS. 10A through 10C are plan views showing various modifications of sensor cells applicable to an air-fuel ratio sensing element having four gas holes in accordance with the first embodiment of the present invention.
Figure 10B:
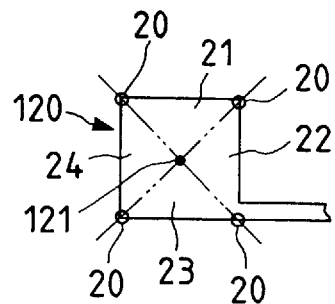
Figure 10C:
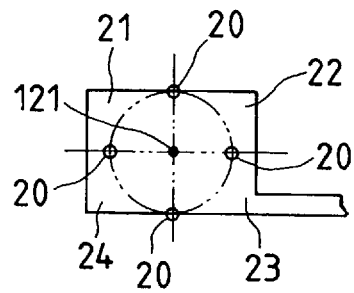

As shown in FIGS. 10A through 10C, according to the first embodiment of the present invention, it is also preferable that the sensor electrode 120 has a square or rectangular (where one half of long side<short side) configuration. A total of four gas hole projection images 20 are formed symmetrically as shown in the drawing.

The sensor electrode 120 is shaped so as to be dividable into four subsections 21, 22, 23 and 24 each having substantially the same area and configuration defined by two virtual straight lines passing through the geometric centroid 121 of sensor electrode 120 and the center 200 (refer to FIG. 3) of each gas hole projection image 20. The geometric centroid 121 of sensor electrode 120 coincides with the midpoint between the centers 200 of opposing two circular gas hole projection images 20.

Figure 11A:
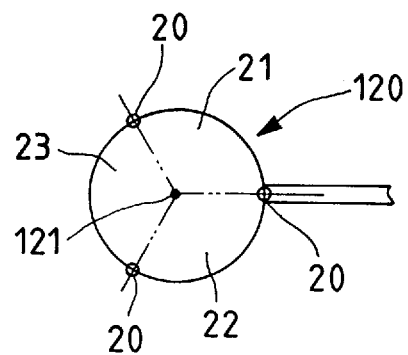
FIGS. 11A and 11B are plan views showing various modifications of sensor cells applicable to an air-fuel ratio sensing element having three gas holes in accordance with the first embodiment of the present invention.
Figure 11B:
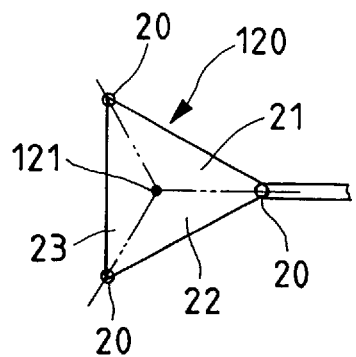

Still further, as shown in FIGS. 11A and 11B, according to the first embodiment of the present invention, it is also preferable that the sensor electrode 120 has a circular or triangular configuration. A total of three gas hole projection images 20 are formed symmetrically as shown in the drawing.

The sensor electrode 120 is shaped so as to be dividable into three subsections 21, 22 and 23 each having substantially the same area and configuration defined by three virtual straight lines each connecting the geometric centroid 121 of sensor electrode 120 and the center 200 (refer to FIG. 3) of each gas hole projection image 20. The distance from the geometric centroid 121 of sensor electrode 120 to the center 200 of one circular gas hole projection images 20 is substantially identical to the distance from the geometric centroid 121 to the center 200 of any other circular gas hole projection image 20.

Figure 12A:
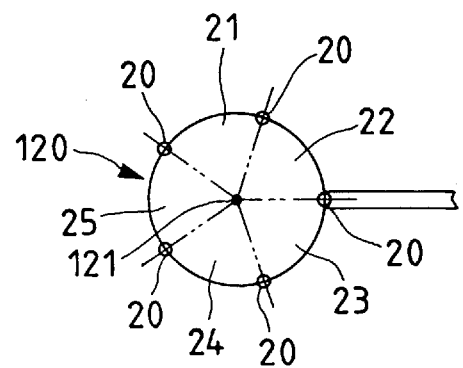
FIGS. 12A and 12B are plan views showing various sensor cells applicable to an air-fuel ratio sensing element having five gas holes in accordance with the first embodiment of the present invention.
Figure 12B:
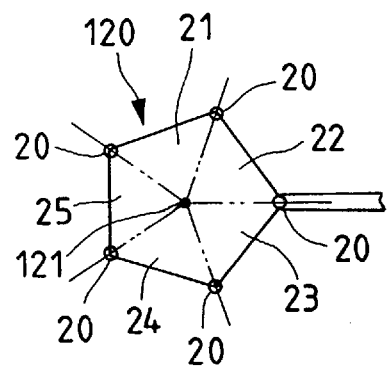

Yet further, as shown in FIGS. 12A and 12B, according to the first embodiment of the present invention, it is also preferable that the sensor electrode 120 has a circular or pentagonal configuration. A total of five gas hole projection images 20 are formed symmetrically as shown in the drawing.

The sensor electrode 120 is shaped so as to be dividable into five subsections 21, 22, 23, 24 and 25 each having substantially the same area and configuration defined by five virtual straight lines each connecting the geometric centroid 121 of sensor electrode 120 and the center 200 (refer to FIG. 3) of each gas hole projection image 20. The distance from the geometric centroid 121 of sensor electrode 120 to the center 200 of one circular gas hole projection images 20 is substantially identical to the distance from the geometric centroid 121 to the center 200 of any other circular gas hole projection image 20.

Embodiment 2

Although the gas hole projection images 20 disclosed in the first embodiment are positioned just on the periphery or outline of the sensor electrode 120, it is also possible to locate these gas hole projection images 20 inward or outward from the periphery or outline of the sensor electrode 120.

The second embodiment of the present invention, as shown in FIGS. 13A through 15, discloses another air-fuel ratio sensing elements having gas hole projection images arranged at various locations.

Figure 13A:
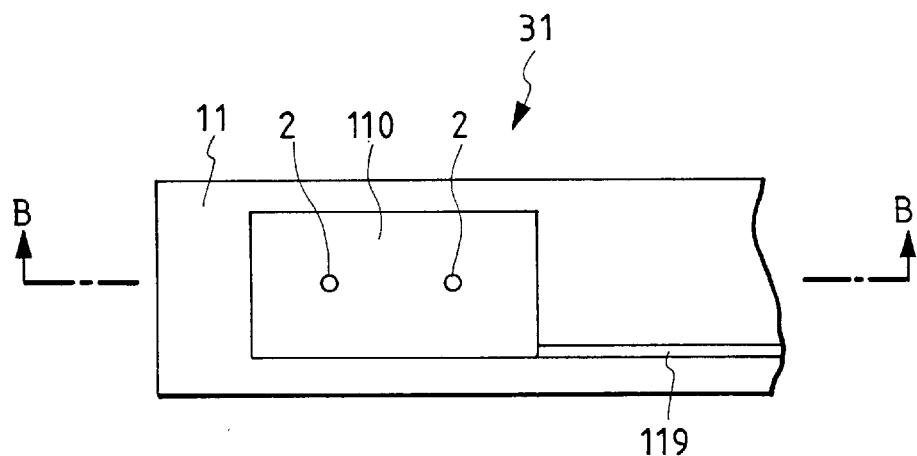
FIG. 13A is a plan view showing an air-fuel ratio sensing element having gas holes positioned within the region of the pump electrodes in accordance with a second embodiment of the present invention.
Figure 13B:
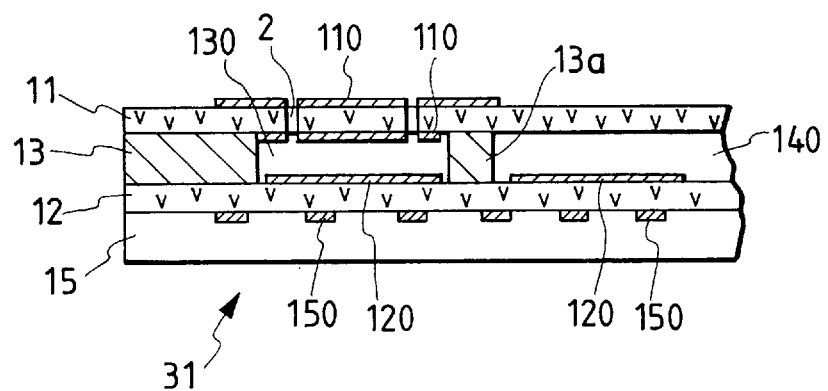
FIG. 13B is a cross-sectional view taken along a line B—B of FIG. 13A.

An air-fuel ratio sensing element 31, shown in FIGS. 13A and 13B, has gas holes 2 formed within the region of pump electrodes 110 of pump cell 11 so as to be positioned completely inward from the periphery or outline of pump electrode 110. The gas holes 2 projected perpendicularly to the surface of sensor cell 12, form their entire projection images within the region of sensor electrode 120. The air-fuel ratio sensing element 31 has first gas chamber 130 and second gas chamber 140 separated by a partition wall portion 13a of spacer 13. Otherwise, the arrangement of the air-fuel ratio sensing element 31 is substantially the same as that of the air-fuel ratio sensing element of the first embodiment.

Figure 14A:
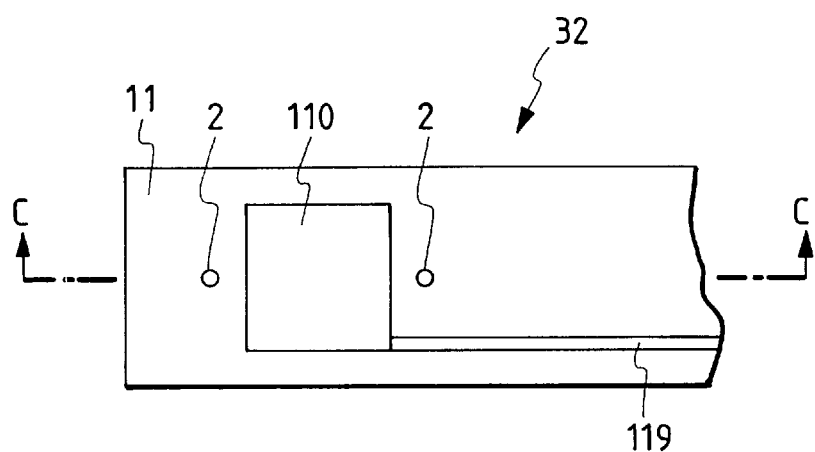
FIG. 14A is a plan view showing an air-fuel ratio sensing element having gas holes positioned outside the region of pump electrodes in accordance with the second embodiment of the present invention.
Figure 14B:
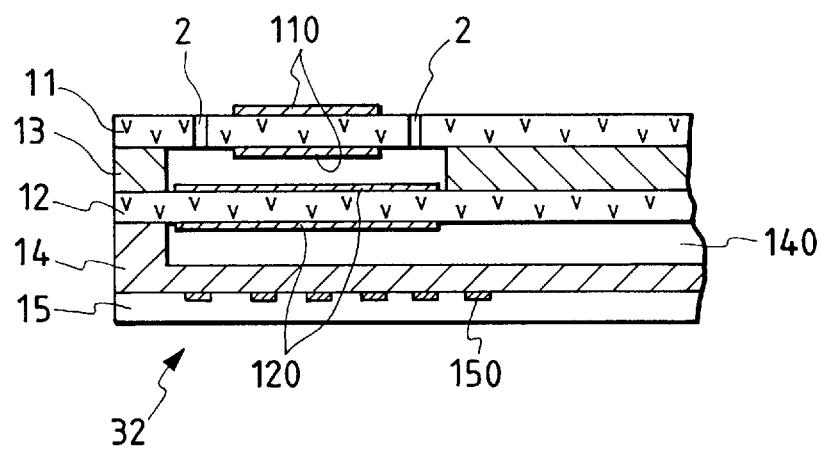
FIG. 14B is a cross-sectional view taken along a line C—C of FIG. 14A.

An air-fuel ratio sensing element 32, shown in FIGS. 14A and 14B, has gas holes 2 directly formed on the pump cell 11 and positioned outside the region of pump electrode 110. Otherwise, the arrangement of the air-fuel ratio sensing element 31 is substantially the same as that of the air-fuel ratio sensing element of the first embodiment.

Figure 15:
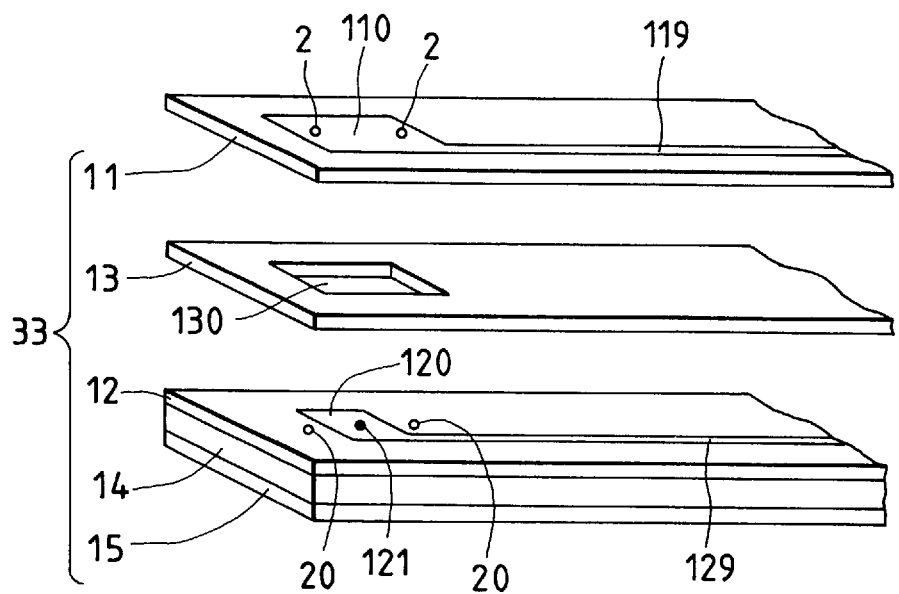
FIG. 15 is a perspective view showing the disassembled air-fuel ratio sensing element having gas hole projection images positioned outside the region of a sensor electrode in accordance with the second embodiment of the present invention.

An air-fuel ratio sensing element 33, shown in FIG. 15, has gas holes 2 whose projection images are formed outside the region of sensor electrode 120 when they are projected perpendicularly to the surface of sensor cell 12.

Otherwise arrangement of this embodiment is substantially the same as that of the air-fuel ratio sensing element of the first embodiment.

Embodiment 3

The third embodiment of the present invention, as shown in FIGS. 16 through 19, discloses air-fuel ratio sensing elements 41 and 42 having pump cell 11 and sensor cell 12 provided on the opposing walls of a gas chamber 430.

Figure 16:
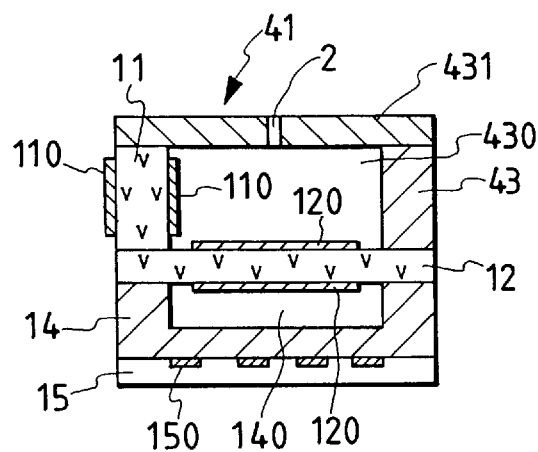
FIG. 16 is a cross-sectional view showing an air-fuel ratio sensing element having a pump cell and a sensor cell disposed on the inside walls of a gas chamber in a non-facing relationship in accordance with a third embodiment of the present invention.
Figure 17:
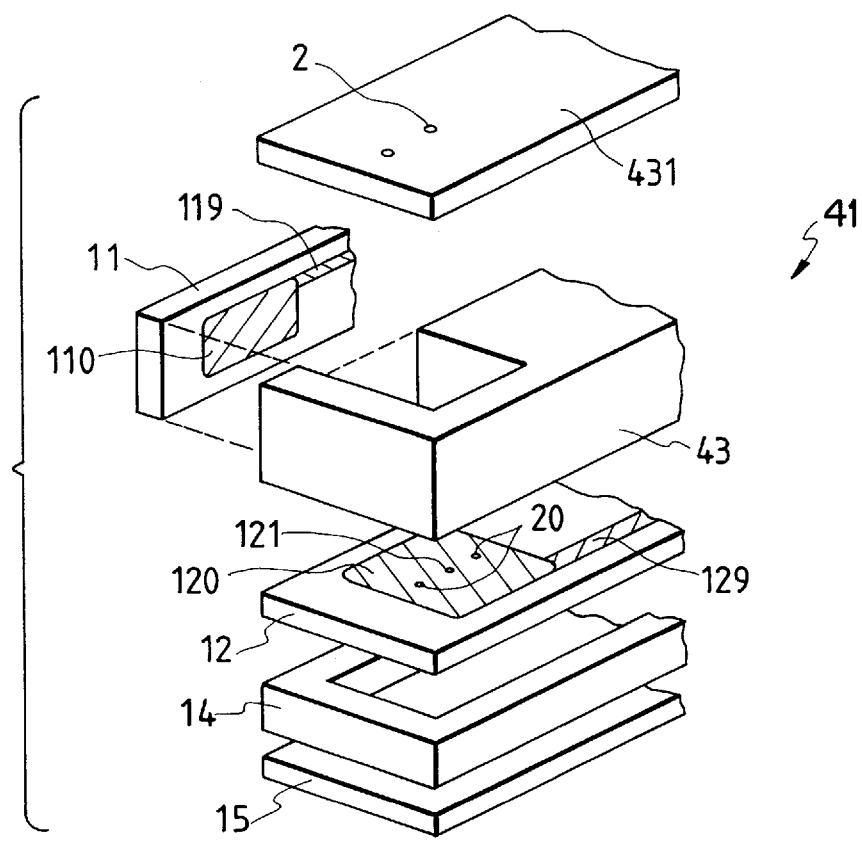
FIG. 17 is a perspective view showing the disassembled air-fuel ratio sensing element shown in FIG. 16.

More specifically, the air-fuel ratio sensing element 41, shown in FIGS. 16 and 17, comprises an inside hollow space serving as gas chamber 430, sensor cell 12 constituting the bottom surface of gas chamber 430, pump cell 11 constituting one side surface of gas chamber 430, and spacers 431 and 43 constituting other inside surfaces of gas chamber 430.

Two gas holes 2, each introducing part of the sensed gas into gas chamber 430, are provided on the spacer 431 which is opposed to the sensor cell 12.

Gas holes 2, when projected perpendicularly to the surface of sensor cell 12, form their projection images 20 on the surface of sensor electrode 120. The sensor electrode 120 is shaped so as to be dividable into two subsections having substantially the same area and configuration defined by a virtual line passing through the center 200 (refer to FIG. 3) of each gas hole projection image 20 and the geometric centroid of sensor electrode 120.

Otherwise, the arrangement of air-fuel ratio sensing element 41 is substantially the same as that of the air-fuel ratio sensing element of the first embodiment.

Figure 18:
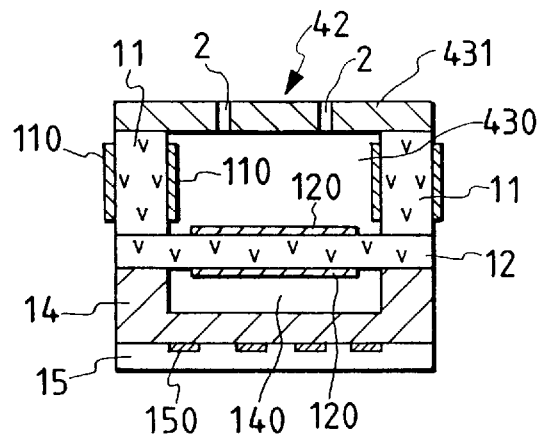
FIG. 18 is a cross-sectional view showing another air-fuel ratio sensing element having a pump cell and a sensor cell disposed on the inside walls of a gas chamber in a non-facing relationship in accordance with the third embodiment of the present invention.
Figure 19:
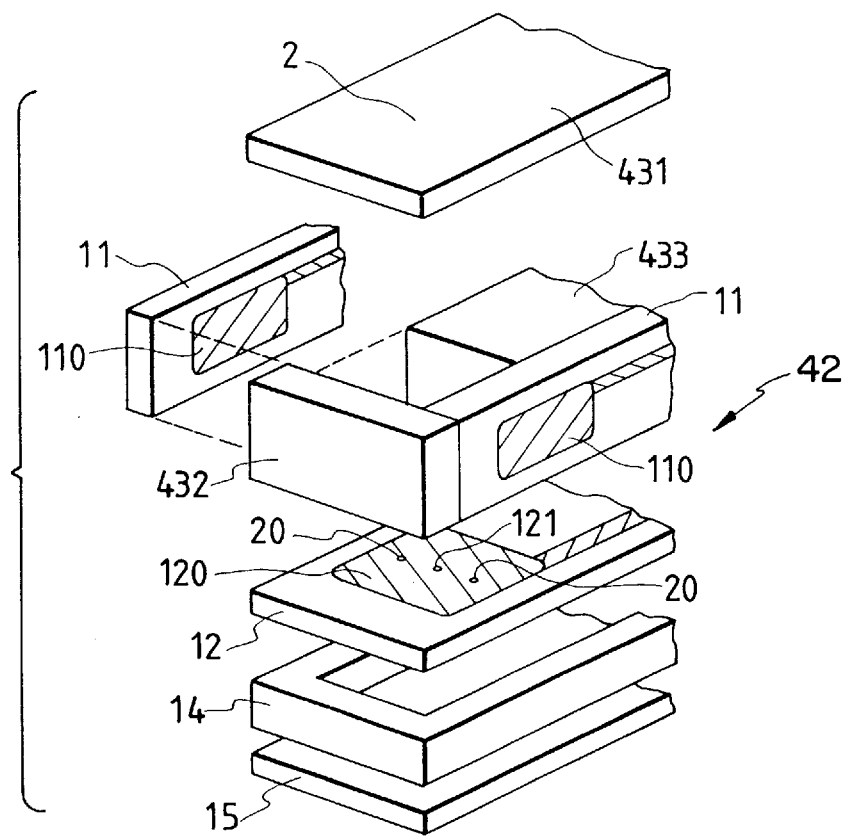
FIG. 19 is a perspective view showing the disassembled air-fuel ratio sensing element shown in FIG. 18.

The air-fuel ratio sensing element 42, shown in FIGS. 18 and 19, comprises an inside hollow space serving as gas chamber 430, sensor cell 12 constituting the bottom surface of gas chamber 430, two separate pump cells 11 constituting opposed side surfaces of gas chamber 430, and spacers 431, 432 and 433 constituting other inside surfaces of gas chamber 430. Otherwise, the arrangement of air-fuel ratio sensing element 42 is substantially the same as that of the above-described air-fuel ratio sensing element 41.

Embodiment 4

Figure 20:
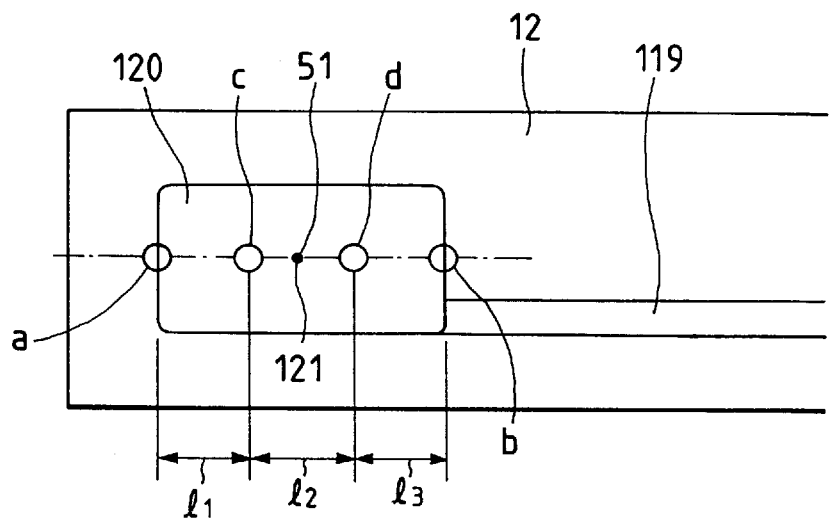
FIG. 20 is a plan view showing a sensor cell of an air-fuel ratio sensing element having four in-line gas holes according to a fourth embodiment of the present invention.

FIG. 20 shows an air-fuel ratio sensing element in accordance with a fourth embodiment of the present invention. This embodiment has a total of four in-line gas holes each introducing part of the sensed gas into the gas chamber. Although not shown in the drawing, the air-fuel ratio sensing element of the fourth embodiment comprises a pump cell having pump electrodes provided on opposite surfaces thereof, sensor cell 12 having sensor electrodes 120 provided on opposite surfaces thereof, and a gas chamber interposed between these cells and having two opposed surfaces defined by these cells, in the same manner as the first embodiment.

The four in-line gas holes formed on the pump cell or pump electrode, when projected perpendicularly to the surface of sensor electrode 120, form their projection images a, b, c, and d each having substantially the same circular area and disposed along a straight line as shown in FIG. 20.

Reference numeral 51 represents the projection image of the geometric centroid of four gas holes, formed when it is projected on the sensor electrode 120. According to this embodiment, projection image 51 of the of the four gas holes coincides with the geometric centroid 121 of sensor electrode 120.

In FIG. 20, $1_1$ represents the distance between two gas holes forming projection images a and c, $1_2$ represents the distance between two gas holes forming projection images c and d, and $1_3$ represents the distance between two gas holes forming projection images d and b. According to the fourth embodiment, $1_1=1_2=1_3=3$ mm. Each circular gas hole has the diameter of approximately 0.1 mm.

Otherwise, the arrangement of this embodiment is substantially the same as that of the air-fuel ratio sensing element of the first embodiment.

Embodiment 5

Figure 21:
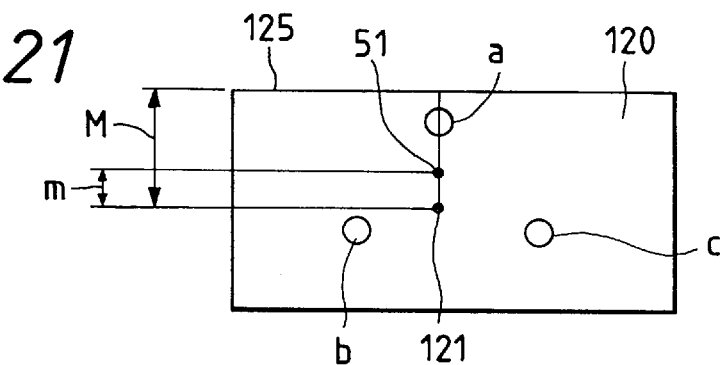
FIG. 21 is a plan view showing a sensor cell of an air-fuel ratio sensing element having three gas holes in accordance with a fifth embodiment of the present invention, wherein the geometric centroid of the sensor electrode and the projection image of the geometric centroid of the three gas holes do not overlap.

FIG. 21 shows an air-fuel ratio sensing element having three gas holes each introducing part of the sensed gas into the gas chamber thereof. The gas holes formed on the pump cell or pump electrode (not shown) are projected perpendicularly to the surface of sensor electrode 120, forming their projection images a, b, and c each having substantially the same circular area.

Reference numeral 51 represents the projection image of the geometric centroid of the triangle defined by three gas holes, formed when it is projected on the sensor electrode 120. According to this embodiment, projection image 51 of the geometrical centroid of the above-defined triangle is offset from the geometric centroid 121 of sensor electrode 12 by the distance m.

In FIG. 21, M represents the smallest distance from the geometric centroid 121 to the periphery or outline 125 of sensor electrode 120 which is positioned in the same side as the projection image 51 with respect to the geometric centroid 121.

According to this embodiment, m is approximately 0.1 mm and M is approximately 1.5 mm, and generally the relationship m≦0.1M is satisfied. The above-described arrangement eliminates any undesirable gradational distribution in the sensed gas concentration along the surface of sensor electrode 120.

Otherwise, the arrangement of this embodiment is the same as that of the air-fuel ratio sensing element of the first embodiment.

Embodiment 6

Figure 22:
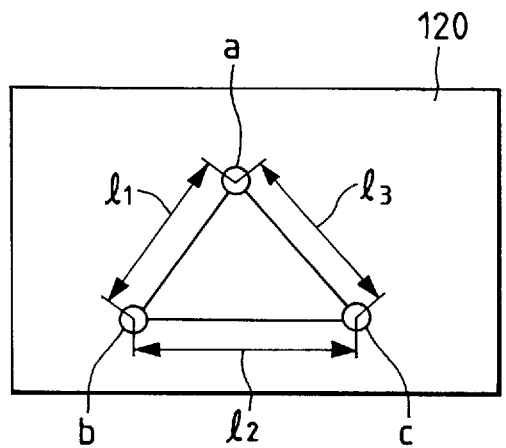
FIG. 22 is a plan view showing a sensor cell of an air-fuel ratio sensing element having three gas holes in accordance with a sixth embodiment of the present invention, wherein the distance between any two gas holes is not identical with the distance between any other two gas holes.
Figure 23:
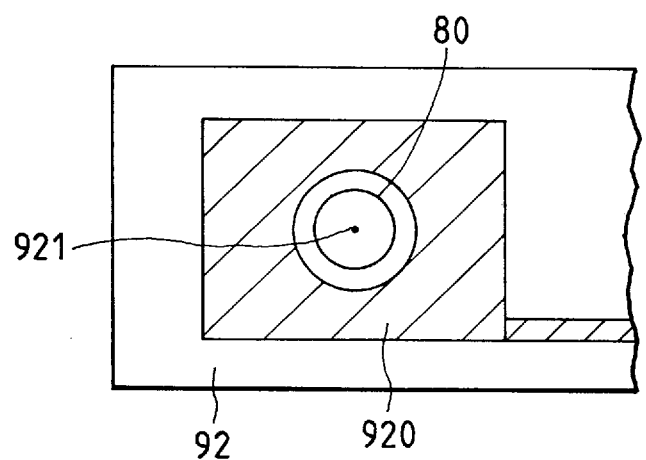
FIG. 23 is a plan view showing a sensor cell of a conventional air-fuel ratio sensing element.

FIG. 22 shows an air-fuel ratio sensing element having three gas holes each introducing part of the sensed gas into the gas chamber thereof. Gas holes formed on the pump cell or pump electrode (not shown) are projected perpendicularly to the surface of sensor electrode 120, forming their projection images a, b, and c each having substantially the same circular area.

In FIG. 22, $1_1$ represents the distance between two gas holes forming projection images a and b, $1_2$ represents the distance between two gas holes forming projection images b and c, and $1_3$ represents the distance between two gas holes forming projection images c and a. According to this embodiment, $1_1$ is approximately 2.3 mm, $1_2$ is approximately 2.5 mm and $1_3$ is approximately 2.6 mm. The mean distance L, in this case, is approximately 2.467 mm. Generally, the distances $1_1$, $1_2$ and $1_3$ are within the range of 0.9L to 1.1L.

Otherwise, the arrangement of the sixth embodiment is substantially the same as that of the air-fuel ration sensing element of the first embodiment.

In view of dispersion among gas holes, the present invention defines the preferable range of these gas holes by the following relationship:

$$0.88R \leq r_n \leq 1.12R$$

where $r_n$ represents the diameter of any one gas hole (see FIG. 3) and R represents the mean value of all the diameters of the gas holes.

As apparent from the foregoing description, the present invention provides an air-fuel ratio sensing element having excellent accuracy and response.

As this invention may be embodied in several forms without departing from the spirit of essential characteristics thereof, the present embodiments described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensing element comprising:
    a pump cell having at least one pair of pump electrodes thereon;
    a sensor cell having a first surface, with a first sensor electrode thereon and having a second sensor electrode; and
    a gas chamber having two surfaces defined by said pump cell and said first surface of said sensor cell, wherein:
    said sensing element defines two to five gas holes communicating with said gas chamber for introducing sensed gas into said gas chamber, said gas holes being substantially identical with each other in their size,
    said gas holes are arranged in such a manner that projection images of said gas holes are formed on said first surface of said sensor cell when said gas holes are projected perpendicularly to said surface of said sensor cell, and
    said gas holes are further arranged such that virtual lines connecting a geometric centroid of said first sensor electrode and geometric centroids of said gas holes define a plurality of similar subsections on said first sensor electrode.

2. The air-fuel ratio sensing element in accordance with claim 1, wherein said subsections of said first sensor electrode satisfy the following relationship:

$$S/s \leq 1.25$$

where S represents an area of a largest subsection and s represents an area of a smallest subsection.

3. The air-fuel ratio sensing element in accordance with claim 1, wherein at least part of the projection image of each gas hole is formed within a region of said first sensor electrode.

4. The air-fuel ratio sensing element in accordance with claim 1, wherein the projection image of each gas hole is entirely formed within a region of said first sensor electrode.

5. An air-fuel ratio sensing element comprising:
    a pump cell having at least one pair of pump electrodes thereon;
    a sensor cell having a first surface, with a first sensor electrode thereon and having a second sensor electrode; and
    a gas chamber having two surfaces defined by said pump cell and said first surface of said sensor cell, wherein:
    said sensing element defines two to five gas holes communicating with said gas chamber for introducing sensed gas into said gas chamber, said gas holes being substantially identical with each other in their size,
    said gas holes are arranged such that projection images of said gas holes are formed on said first surface of said sensor cell when said gas holes are projected perpendicularly to said surface of said sensor cell,
    geometric centroids of said gas holes cooperatively define a maximum configuration, and
    said maximum configuration has a geometric centroid whose projection image coincides with a geometric centroid of said first sensor electrode when said maximum configuration is projected perpendicularly to said first surface of said sensor cell.

6. The air-fuel ratio sensing element in accordance with claim 5, wherein a total number of said gas holes is any one of three, four or five, and a distance between arbitrarily selected two adjacent gas holes is identical with a distance between any other adjacent two gas holes.

7. The air-fuel ratio sensing element in accordance with claim 5, wherein at least part of the projection image of each gas hole is formed within a region of said first sensor electrode.

8. The air-fuel ratio sensing element in accordance with claim 5, wherein the projection image of each gas hole is entirely formed within a region of said first sensor electrode.

9. An air-fuel ratio sensing element comprising:
    a pump cell having at least one pair of pump electrodes thereon;

a sensor cell having a first surface, with a first sensor electrode thereon and having a second sensor electrode; and a gas chamber having two surfaces defined by said pump cell and said first surface of said sensor cell, wherein:

said sensing element defines two to five gas holes communicating with said gas chamber for introducing sensed gas into said gas chamber, said gas holes being substantially identical with each other in their size, said gas holes are arranged such that projection images of said gas holes are formed on said first surface of said sensor cell when said gas holes are projected perpendicularly to said surface of said sensor cell, said gas holes cooperatively define a maximum configuration, said maximum configuration has a geometric centroid whose projection image is formed on said first sensor electrode when said maximum configuration is projected perpendicularly to said first surface of said sensor cell, and said gas holes and said first sensor electrode cooperatively satisfy the following relationship:

$$m \leq 0.1M$$

where m represents an offset amount from the projection image of said geometric centroid of said maximum configuration to a geometric centroid of said first sensor electrode, while M represents a smallest distance from said geometric centroid of said first sensor electrode to a periphery of said first sensor electrode positioned in the same side as said projection image of said geometric centroid of said maximum configuration.

10. The air-fuel ratio sensing element in accordance with claim 9, wherein said gas holes cooperatively satisfy the following relationship:

$$0.88R < r_n < 1.12R$$

where $r_n$ represents a diameter of any one of said gas holes, while R represents a mean value of all diameters of said gas holes.

11. The air-fuel ratio sensing element in accordance with claim 9, wherein a total number of said gas holes is any one of three, four and five, and said gas holes cooperatively satisfy the following relationship:

$$0.9L \leq 1n \leq 1.1L$$

where 1n represents a distance between any two adjacent gas holes and L represents a mean value of all distances between two adjacent gas holes.

12. The air-fuel ratio sensing element in accordance with claim 9, wherein at least part of the projection image of each gas hole is formed within a region of said first sensor electrode.

13. The air-fuel ratio sensing element in accordance with claim 9, wherein the projection image of each gas hole is entirely formed within a region of said first sensor electrode.

* * * * *